US008901199B2

(12) United States Patent
Vu et al.

(10) Patent No.: US 8,901,199 B2
(45) Date of Patent: *Dec. 2, 2014

(54) COMPOSITIONS AND METHODS FOR UV-CURABLE COSMETIC NAIL COATINGS

(75) Inventors: Thong Vu, Vista, CA (US); Chad Conger, San Marcos, CA (US); Diane Marie Larsen, Carlsbad, CA (US); David Valia, San Diego, CA (US); Douglas D. Schoon, Dana Point, CA (US)

(73) Assignee: Creative Nail Design, Inc., Vista, CA (US)

( * ) Notice: Subject to any disclaimer, the term of this patent is extended or adjusted under 35 U.S.C. 154(b) by 326 days.

This patent is subject to a terminal disclaimer.

(21) Appl. No.: 13/042,436

(22) Filed: Mar. 7, 2011

(65) Prior Publication Data

US 2011/0274633 A1 Nov. 10, 2011

Related U.S. Application Data

(63) Continuation of application No. 12/555,571, filed on Sep. 8, 2009, now Pat. No. 8,263,677, and a continuation of application No. 12/573,633, filed on Oct. 5, 2009, now Pat. No. 8,492,454, and a continuation of application No. 12/573,640, filed on Oct. 5, 2009, now Pat. No. 8,541,482.

(51) Int. Cl.
| | |
|---|---|
| *C08F 20/18* | (2006.01) |
| *A61L 27/56* | (2006.01) |
| *C08J 3/09* | (2006.01) |
| *C09D 4/06* | (2006.01) |
| *A61K 8/73* | (2006.01) |
| *A61K 8/46* | (2006.01) |
| *A61Q 3/02* | (2006.01) |
| *A61K 8/81* | (2006.01) |
| *A61K 8/87* | (2006.01) |
| *A61K 8/86* | (2006.01) |

(52) U.S. Cl.
CPC ... *A61K 8/46* (2013.01); *C09D 4/06* (2013.01); *A61K 8/731* (2013.01); *A61Q 3/02* (2013.01); *A61K 8/8147* (2013.01); *A61K 8/8135* (2013.01); *A61K 8/87* (2013.01); *A61K 8/8152* (2013.01); *A61K 8/86* (2013.01)
USPC .............. 522/182; 522/49; 522/90; 522/96; 522/120; 522/121; 424/61; 424/401

(58) Field of Classification Search
USPC ............ 521/144, 149; 424/61, 401; 522/182, 522/90, 96, 120, 121
See application file for complete search history.

(56) References Cited

U.S. PATENT DOCUMENTS

| | | |
|---|---|---|
| 1,548,497 A | 8/1925 | Weeks |
| 1,743,922 A | 1/1930 | Kirlin |
| 1,900,761 A | 3/1933 | Proteau |
| 1,947,153 A | 2/1934 | Dellinger |
| 2,979,061 A | 4/1961 | Greenman |
| 3,297,664 A | 1/1967 | Miskel |
| 3,629,187 A | 12/1971 | Waller |
| 3,709,866 A | 1/1973 | Waller |
| 3,928,113 A | 12/1975 | Rosenberg |
| 4,089,763 A | 5/1978 | Dart |
| 4,158,053 A | 6/1979 | Greene et al. |
| 4,174,307 A | 11/1979 | Rowe |
| 4,189,365 A | 2/1980 | Schmitt |
| 4,205,018 A | 5/1980 | Nagasawa |
| 4,229,431 A | 10/1980 | Lee, Jr. |
| 4,260,701 A | 4/1981 | Lee, Jr. |
| 4,421,881 A | 12/1983 | Benkendorf |
| 4,424,252 A | 1/1984 | Nativi |
| 4,514,527 A | 4/1985 | Bowen |
| 4,521,550 A | 6/1985 | Bowen |
| 4,572,888 A | 2/1986 | Maeda |
| 4,574,138 A | 3/1986 | Moran, Jr. |
| 4,596,260 A | 6/1986 | Giuliano |
| 4,600,030 A | 7/1986 | Newman |
| 4,666,952 A | 5/1987 | Henne |
| 4,682,612 A | 7/1987 | Giuliano |
| 4,690,369 A | 9/1987 | Giuliano |
| 4,692,396 A | 9/1987 | Uchida |
| 4,704,303 A | 11/1987 | Cornell |
| 4,718,957 A | 1/1988 | Sensenbrenner |
| 4,721,735 A | 1/1988 | Bennett |
| 4,745,003 A | 5/1988 | Sirkoch |
| 4,766,005 A | 8/1988 | Montgomery |
| 4,775,580 A | 10/1988 | Dighton |
| 4,813,875 A | 3/1989 | Hare |

(Continued)

FOREIGN PATENT DOCUMENTS

| | | |
|---|---|---|
| EP | 0356868 | 3/1990 |
| EP | 0453628 | 10/1991 |

(Continued)

OTHER PUBLICATIONS

Data Sheet for Diurethane Dimethacrylate from Esstech, Inc., 2011.

(Continued)

*Primary Examiner* — Kara Boyle
(74) *Attorney, Agent, or Firm* — Venable LLP; Keith G. Haddaway; Daniel A. Kopp

(57) ABSTRACT

The present disclosure relates generally to compositions for natural and artificial nail coatings, and particularly, but not by way of limitation, to polymerizable compositions that provide improved adhesion-promoting and improved solvent-susceptibility.

34 Claims, No Drawings

(56) References Cited

U.S. PATENT DOCUMENTS

| | | |
|---|---|---|
| 4,844,102 A | 7/1989 | Repensek |
| 4,846,165 A | 7/1989 | Hare |
| 4,863,993 A | 9/1989 | Montgomery |
| 4,867,680 A | 9/1989 | Hare |
| 5,026,780 A | 6/1991 | Takizawa |
| 5,063,257 A | 11/1991 | Akahane |
| 5,071,888 A | 12/1991 | Kubota |
| 5,118,495 A | 6/1992 | Nafziger |
| 5,127,414 A | 7/1992 | Mast |
| 5,173,288 A | 12/1992 | Everhart et al. |
| 5,177,120 A | 1/1993 | Hare |
| 5,194,292 A | 3/1993 | Billings |
| 5,206,011 A | 4/1993 | Pappas |
| 5,219,965 A | 6/1993 | Valint, Jr. |
| 5,229,431 A | 7/1993 | Pinchuk |
| 5,270,351 A | 12/1993 | Bowen |
| 5,314,683 A | 5/1994 | Schlossman |
| 5,328,725 A | 7/1994 | Sato |
| 5,338,769 A | 8/1994 | Miyamoto |
| 5,344,583 A | 9/1994 | Bayless |
| 5,407,666 A | 4/1995 | Patel |
| 5,415,903 A | 5/1995 | Hoffman |
| 5,424,061 A | 6/1995 | Pappas |
| 5,426,166 A | 6/1995 | Usifer |
| 5,435,994 A | 7/1995 | Valenty |
| 5,453,451 A | 9/1995 | Sokol |
| 5,456,905 A | 10/1995 | Valenty |
| 5,484,864 A | 1/1996 | Usifer |
| 5,516,509 A | 5/1996 | Marr-Leisy |
| 5,637,292 A | 6/1997 | Thomas |
| 5,662,891 A | 9/1997 | Martin |
| 5,690,840 A | 11/1997 | Antonucci et al. |
| 5,690,940 A | 11/1997 | Joo |
| 5,698,371 A | 12/1997 | Mirle |
| 5,708,052 A | 1/1998 | Fischer |
| 5,720,804 A | 2/1998 | Martin |
| 5,785,958 A | 7/1998 | Sirdesai |
| 5,792,447 A | 8/1998 | Socci |
| 5,824,373 A | 10/1998 | Biller |
| 5,849,853 A | 12/1998 | Schade |
| 5,871,573 A | 2/1999 | Cook et al. |
| 5,958,951 A | 9/1999 | Ahrndt |
| 5,965,111 A | 10/1999 | Ellingson |
| 5,965,147 A | 10/1999 | Steffier |
| 5,985,951 A | 11/1999 | Cook |
| 5,985,998 A | 11/1999 | Sommerfeld |
| 5,994,530 A | 11/1999 | Posey-Dowty |
| 5,998,495 A | 12/1999 | Oxman |
| 6,015,549 A | 1/2000 | Cowperthwaite |
| 6,020,402 A | 2/2000 | Anand |
| 6,121,381 A | 9/2000 | Deguchi |
| 6,147,137 A | 11/2000 | Jia |
| 6,238,679 B1 | 5/2001 | delaPoterie |
| 6,239,189 B1 | 5/2001 | Narayan |
| 6,251,520 B1 | 6/2001 | Blizzard et al. |
| 6,254,878 B1 | 7/2001 | Bednarek et al. |
| 6,255,034 B1 | 7/2001 | Shimada |
| 6,355,599 B1 | 3/2002 | Zahora |
| 6,391,938 B1 | 5/2002 | Lilley |
| 6,413,696 B1 | 7/2002 | Pang |
| 6,426,034 B1 | 7/2002 | McComas |
| 6,481,444 B1 | 11/2002 | Lilley |
| 6,599,958 B2 | 7/2003 | Lilley |
| 6,685,838 B2 | 2/2004 | Licata |
| 6,750,277 B1 | 6/2004 | Yamana |
| 6,803,394 B2 | 10/2004 | Lilley |
| 6,818,207 B1 | 11/2004 | Schoon |
| 6,831,115 B2 | 12/2004 | Williams |
| 7,063,936 B2 | 6/2006 | Kakino |
| 7,098,256 B2 | 8/2006 | Ong |
| 7,125,591 B2 | 10/2006 | Nakajima et al. |
| 7,309,550 B2 | 12/2007 | Rach |
| 7,364,834 B2 | 4/2008 | Barr |
| 7,378,460 B2 | 5/2008 | Schmidt |
| 7,388,039 B2 | 6/2008 | Williams |
| 7,514,477 B2 | 4/2009 | Klare |
| 7,595,351 B2 | 9/2009 | Hayes |
| 7,615,283 B2 | 11/2009 | Radcliffe |
| 7,649,058 B2 | 1/2010 | McCabe |
| 7,713,680 B2 | 5/2010 | Ito |
| 7,718,264 B2 | 5/2010 | Klun |
| 7,722,939 B2 | 5/2010 | Schwantes |
| 7,806,050 B2 | 10/2010 | Nakamura |
| 2001/0007676 A1 | 7/2001 | Mui et al. |
| 2002/0156144 A1 | 10/2002 | Williams |
| 2003/0019501 A1 | 1/2003 | Hirota |
| 2003/0134932 A1 | 7/2003 | Lehmann |
| 2003/0175225 A1 | 9/2003 | Leacock et al. |
| 2003/0220416 A1 | 11/2003 | Montgomery |
| 2004/0249014 A1 | 12/2004 | Williams |
| 2005/0002878 A1 | 1/2005 | Lefrancois et al. |
| 2006/0005772 A1 | 1/2006 | Shin |
| 2006/0039939 A1 | 2/2006 | Lai |
| 2006/0128833 A1 | 6/2006 | Itoh et al. |
| 2006/0189728 A1 | 8/2006 | Qian |
| 2007/0021533 A1 | 1/2007 | Yan |
| 2007/0099119 A1 | 5/2007 | Rach |
| 2007/0106017 A1 | 5/2007 | Kessel |
| 2008/0149270 A1 | 6/2008 | Oshima |
| 2008/0167399 A1 | 7/2008 | Utterodt |
| 2008/0213506 A1 | 9/2008 | Eu |
| 2008/0241083 A1 | 10/2008 | Schoon |
| 2009/0086492 A1 | 4/2009 | Meyer |
| 2009/0220436 A1 | 9/2009 | Anderson et al. |
| 2010/0012263 A1 | 1/2010 | Oshima |
| 2010/0105289 A1 | 4/2010 | Yonezu |
| 2011/0045036 A1 | 2/2011 | Lintner et al. |

FOREIGN PATENT DOCUMENTS

| | | |
|---|---|---|
| EP | 0426085 | 5/1992 |
| EP | 0545116 | 6/1993 |
| EP | 943310 | 3/2002 |
| EP | 1479364 | 11/2004 |
| EP | 1450755 | 8/2008 |
| GB | 656264 | 8/1951 |
| JP | 5271460 | 10/1993 |
| KR | 970002606 | 3/1997 |
| WO | 9312759 | 7/1993 |
| WO | 9848769 | 11/1998 |
| WO | 9955290 | 11/1999 |
| WO | 0236637 | 5/2002 |
| WO | 2004030801 | 4/2004 |
| WO | 2008082929 | 7/2008 |
| WO | 2009005975 | 1/2009 |
| WO | 2011011304 | 1/2011 |

OTHER PUBLICATIONS

Data Sheet for Polypropylene Glycol Monomethacrylate. Sartomer. 2011.
Ebecryl 220 Data Sheet. Lookchem. 2008.
International Preliminary Report on Patentability issued in International Application No. PCT/US2010/047169 dated Apr. 11, 2012.
International Preliminary Report on Patentability issued in International Application No. PCT/US2010/047165 dated Mar. 13, 2012.
International Preliminary Report on Patentability issued in International Application No. PCT/US2010/047171 dated Apr. 11, 2012.
International Search Report for PCT International Application No. PCT/US2011/027455, mailed May 9, 2011.
Office Action issued in U.S. Appl. No. 12/555,571 dated May 17, 2011.
Office Action issued in U.S. Appl. No. 12/555,571 dated Oct. 26, 2011.
Office Action issued in U.S. Appl. No. 12/573,633 dated Feb. 13, 2012.
Office Action issued in U.S. Appl. No. 12/573,633 dated May 24, 2011.
Office Action issued in U.S. Appl. No. 12/573,640 dated Aug. 15, 2012.
Office Action issued in U.S. Appl. No. 13/079,261 dated Jun. 14, 2012.

(56) References Cited

OTHER PUBLICATIONS

Office Action issued in U.S. Appl. No. 13/079,261 dated Oct. 14, 2011.
Office Action issued in U.S. Appl. No. 13/303,584 dated Oct. 22, 2012.
Cheremisinoff, N.P. "Handbook of Hazardous Chemical Properties," Copyright 2000, Elsevier, p. 211.
International Search Report for PCT International Application No. PCT/US2010/147171, mailed Nov. 10, 2010.
Kumar, Sudesh G, et al., Biodegradation of gelatin-g-Poly (ethyl Acrylate) copolymers, 26 Journal of Applied Polymer Science, (1981) 3633-3641.
Physical Properties of Monomers, "Diurethane Dimethacrylate (isomers)." Polymer Handbook, 4th Edition, 1999, John Wiley & Sons.
Venz S. et al., Modified Surface-Active Monomers for Adhesive Binding to Dentin, vol. 72, No. 3 Journal of Dental Research, Mar. 1993, pp. 582-586.
International Search Report for PCT International Application No. PCT/US2010/047165, mailed Feb. 25, 2011.
International Search Report for PCT International Application No. PCT/US2010/047169, mailed Nov. 9, 2010.

US 8,901,199 B2

COMPOSITIONS AND METHODS FOR UV-CURABLE COSMETIC NAIL COATINGS

The present application is a continuation-in-part of application Ser. No. 12/555,571, filed Sep. 8, 2009; of application Ser. No. 12/573,633, filed Oct. 5, 2009; and of application Ser. No. 12/573,640, filed Oct. 5, 2009. The entire content of each parent application is incorporated by reference for all purposes. The present application incorporates by reference in its entirety and for all purposes, U.S. Pat. No. 6,818,207, assigned to the assignee of the present invention.

FIELD OF THE INVENTION

The present disclosure relates generally to compositions for nail coatings, and particularly, but not by way of limitation, to polymerizable compositions that provide improved adhesion, durability/toughness, and scratch resistance, as well as improved solvent removability.

BACKGROUND

The information provided below is not admitted to be prior art to the present invention, but is provided solely to assist the understanding of the reader.

Artificial fingernail and toenail compositions in the form of nail coatings and enhancements are well known and have become a major product line in the appearance and beauty industry. The appearance of one's fingernails (and in many cases also toenails) has become of importance to many fashion conscious individuals or those who wish to correct physical deformities to the natural nail. Commercial artificial nail compositions have been used to enhance the appearance of nails and also to enhance the physical properties of nails, including strengthening fragile nail surface.

Conventional nail coatings may be classified into two categories: nail polishes; also known as lacquers, varnish or enamels and artificial nails; also known as gels or acrylics. Nail polishes typically comprise various solid components which are dissolved and/or suspended in non-reactive solvents. Upon application and drying, the solids deposit on the nail surface as a clear, translucent or colored film. Typically, nail polishes are easily scratched and are easily removable with solvent, usually within one minute and if not removed as described, will chip or peel from the natural nail in one to five days.

Conventional artificial nails are comprised of chemically reactive monomers, and/or oligomers, in combination with reactive or non-reactive polymers to create systems which are typically 100% solids and do not require non-reactive solvents. Upon pre-mixing and subsequent application to the nail plate, or application and exposure to UV radiation, a chemical reaction ensues resulting in the formation of long lasting, highly durable cross-linked thermoset nail coating that is difficult to remove. Artificial nails may possess greatly enhanced adhesion, durability, as well as scratch and solvent resistance when compared to nail polishes. However, because of these inherent properties, such thermosets are much harder to remove, should the consumer so desire. Removal typically requires soaking in non-reactive solvents for 30-90 minutes (for acrylics and currently available "soakable gels"; it may take more than 90 minutes if ever to remove traditional UV nail gels by solvent) and typically may also require heavily abrading the surface or scraping with a wooden or metal probe to assist the removal process.

There remains a need for a cosmetic product that possesses the enhanced adhesion properties and durability of thermosets, yet also possesses the ease of removal more similar to that of nail polishes.

Other objects and advantages will become apparent from the following disclosure.

SUMMARY OF INVENTION

An aspect of the present disclosure provides a removable nail coating comprising a 3-dimentional (3-D) thermoset lattice interdispersed within a network comprising an organic solvent-dissolvable resin. According to an aspect of the disclosure, the 3-D thermoset lattice provides enhanced adhesion, durability/toughness, and scratch resistance over conventional artificial nail coatings. According to an aspect of the disclosure, an interconnected system of voids and a network of an organic solvent-dissolvable resin provides ease of solvent removability as compared to conventional nail enhancements.

According to an aspect, the present disclosure provides a liquid composition comprising at least one monomer, and/or oligomer, and/or polymer which polymerize to a 3-D thermoset. According to an aspect, the present disclosure provides a liquid composition comprising at least one organic solvent-dissolvable resin. According to an aspect, the organic solvent-dissolvable resin forms a network of inclusions within the 3-D thermoset lattice.

According to an aspect, the present disclosure provides an adhesion-promoting nail coating composition having increased sensitivity to solvent. According to an aspect, the present disclosure provides a removable, adhesion-promoting nail coating composition comprising a polyalkaleneglycol (meth)acrylate and a non-reactive solvent. According to an aspect, the present disclosure provides a removable, adhesion-promoting nail coating composition comprising a polymerizable polyol modified (meth)acrylate resin and a non-reactive solvent.

According to an aspect, the present disclosure provides a liquid composition comprising at least one polymer which is incorporated within the 3-D lattice, which both conveys enhanced adhesion and facilitates solvent removal of the polymer. According to an aspect, the polymer which conveys both enhanced adhesion and which facilitates solvent removal of the polymer is a polymer co-polymerized from methyl methacrylate (MMA) and methacrylic acid (MAA) to form a polymer composed of polymethyl methacrylate (PMMA) and polymethacrylic acid (PMAA). According to an aspect, the monomeric portions of the polymer are present in a ratio of 90 parts PMMA to 10 parts PMAA (90:10 PMMA/PMAA). According to an aspect, the MAA or MMA monomer fraction in the polymerization may vary from 0 to 100%.

According to an aspect, the present disclosure provides a monomer which confers the property of ease of removal of the polymerized lattice by providing solvent-sensitive sites in the cured thermoset. According to an aspect, suitable monomers may include any acrylated or methacrylated monomer in the polyethyleneglycol (PEG), polypropyleneglycol (PPG), and polybutyleneglycol (PBG) families. According to an aspect, the monomer may be polypropylene glycol-4-monomethacrylate (PPG4 monomethacrylate) or polypropylene glycol-5-monomethacrylate (PPG5 monomethacrylate). According to an aspect, the solvent-sensitive monomers are present at from about 0 to about 70 (wt %).

According to an aspect, the liquid composition comprises reactive monomers, and/or oligomers, and/or polymers which provide the polymerized composition increased adhesion. According to an aspect, such reactive monomers, and/or oligomers, and/or polymers may be a (meth)acrylate. According to an aspect, the monomer may be a single or mixed acrylate, a single or mixed methacrylate, or a mixture of acrylates and methacrylates. As is known to persons of skill in the polymer arts, the term (meth)acrylate encompasses acrylates and/or methacrylates. According to an aspect, such reactive monomers, and/or oligomers, and/or polymers may be selected from the group consisting of hydroxyethylmethacrylate (HEMA), hydroxypropylmethacrylate (HPMA), Ethyl Methacrylate (EMA), Tetrahydrofurfuryl Methacrylate (THFMA), pyromellitic dianhydride di(meth)acrylate, pyromellitic dianhydride glyceryl dimethacrylate, pyromellitic dimethacrylate, methacroyloxyethyl maleate, 2-hydroxyethyl methacrylate/succinate,1,3-glycerol dimethacrylate/succinate adduct, phthalic acid monoethyl methacrylate, and mixtures thereof. According to an aspect, such reactive monomers, and/or oligomers, and/or polymers possess acidic functionality. According to an aspect, the monomer, oligomer or polymer which provides the polymerized composition increased adhesiveness is present from about 0 to about 80 wt %.

An aspect of the present disclosure provides a polymerizable liquid composition comprising a non-reactive, solvent-dissolvable polymer. According to an aspect, the non-reactive, solvent-dissolvable polymer is a cellulose ester. According to a particular aspect, the non-reactive, solvent-dissolvable polymer is a cellulose acetate alkylate. According to a more particular aspect, the non-reactive, solvent-dissolvable, polymer is a cellulose acetate butyrate or a cellulose acetate propionate. According to a further aspect, the ingredient which provides for ease of removal may be present at from about 0 to about 75 wt %.

An aspect of the present disclosure provides a method of removal. According to an aspect, the thermoset polymerized from the disclosed composition is provided increased sensitivity to organic solvents and, in particular, to acetone. According to an aspect, the composition comprises monomers and oligomers chosen such that various bonds within the resulting thermoset are provided an increased sensitivity to solvent.

According to an aspect of the disclosure, means are provided to distribute organic solvent within the interior of the thermoset matrix and to the polymer/nail interface. According to an aspect, delivering an appropriate solvent to the interior of the thermoset matrix and to the polymer/nail interface will result in a rapid disruption of the adhesive bond interface and greatly facilitates quick and gentle removal from the nail.

An aspect of the present disclosure provides a removable, adhesion-promoting nail coating composition comprising solvent-sensitive monomers and oligomers which retain an ability to be solvated when incorporated into a polymer.

An aspect of the present disclosure provides a removable, adhesion-promoting nail coating composition comprising a plasticizer.

An aspect of the present disclosure provides a removable, adhesion-promoting nail coating composition comprising a photoinitiator.

An aspect of the present disclosure provides a removable, adhesion-promoting nail coating composition comprising a UV-absorber.

An aspect of the present disclosure provides a removable, adhesion-promoting nail coating composition comprising a filler.

An aspect of the present disclosure provides a removable, adhesion-promoting nail coating composition comprising a colorant.

An aspect of the present disclosure provides a removable, adhesion-promoting nail coating composition comprising a rheology modifier.

An aspect of the present disclosure provides a method of improving adhesion of a nail acrylic to a nail surface, the method comprising adding at least one multi-carbonyl-vinyl containing monomer to a polymerizable composition and polymerizing said composition.

An aspect of the present disclosure provides a composition for improving the adhesion of an acrylic polymer to a proteinaceous surface comprising a polymerizable polyol modified [urethane] (meth)acrylate resin, a multicarbonyl-vinyl monomer, and a non-reactive solvent.

Still other aspects and advantages of the present invention will become readily apparent by those skilled in the art from the following detailed description, wherein it is shown and described preferred embodiments of the invention, simply by way of illustration of the best mode contemplated of carrying out the invention. As will be realized, the invention is capable of other and different embodiments, and its several details are capable of modifications in various obvious respects, without departing from the invention. Accordingly, the description is to be regarded as illustrative in nature and not as restrictive.

BRIEF DESCRIPTION OF DRAWINGS

Not Applicable

DETAILED DESCRIPTION OF A PREFERRED EMBODIMENT

Nail coatings commonly consist of a material applied to a keratin nail surface. Prior art coatings may damage the nail by at least two mechanisms. First, adequate adhesion of the enhancement to the nail may require abrasion to roughen the nail surface. And second, removal of the enhancement may require prolonged exposure to possibly damaging solvents and or further abrasion of the nail surface.

An embodiment of the present disclosure provides a removable nail coating comprising a 3-dimentional (3-D) thermoset lattice interdispersed within network comprising an organic solvent-dissolvable resin. According to an aspect of the disclosure, a 3-D thermoset lattice provides enhanced adhesion, durability/toughness, and scratch-resistance over conventional artificial nail coatings.

According to an aspect, the disclosure provides a basecoat that is interposed between the nail surface and a color layer. According to an aspect, the disclosure provides a color layer that is applied to an exposed surface of a basecoat. According to an aspect, the disclosure provides a protective topcoat that is applied to an exposed surface of a color layer.

The terms "nail" and "nail surface" mean the natural, keratinaceous nail surface, or a natural nail to which an artificial nail or nail tip is adhered. In other words, the polymerizable compositions of the invention may be applied directly to the keratinaceous surface of the natural nail, or to a nail surface having affixed thereto an artificial nail or nail tip enhancement.

The invention comprises a polymerizable composition for application to the nails and polymerization thereon to yield an artificial nail structure. The polymerizable composition is preferably an anhydrous liquid, having the consistency of a semi-mobile gel to freely mobile liquid at room temperature. Immediately prior to use, the polymerizable composition is applied to the nail surface and shaped by the nail technician. After polymerization an artificial nail structure is obtained.

An embodiment of the liquid composition comprises reactive monomers, and/or oligomers, and/or polymers which provides the polymerized composition increased adhesion. In certain embodiments, such reactive monomers, and/or oligomers, and/or polymers may be a (meth)acrylate. As is known to persons of skill in the polymer arts, the term (meth)acrylate encompasses acrylates and/or methacrylates. According to an aspect, such reactive monomers, and/or oligomers, and/or polymers may be selected from the group consisting of hydroxypropyl methacrylate (HPMA), hydroxyethyl methacrylate (HEMA), EMA, THFMA, pyromellitic dianhydride di(meth)acrylate, pyromellitic dianhydride glyceryl dimethacrylate, pyromellitic dimethacrylate, methacroyloxyethyl maleate, 2-hydroxyethyl methacrylate/succinate,1, 3-glycerol dimethacrylate/succinate adduct, phthalic acid monoethyl methacrylate, and mixtures thereof. According to an aspect, such reactive monomers, and/or oligomers, and/or polymers possess acidic functionality. According to an aspect, the monomer, oligomer or polymer which provides the polymerized composition increased adhesiveness is present from about 0 to about 50 wt %.

The ethylenically unsaturated reactant may be mono-, di-, tri-, or poly-functional as regards the addition-polymerizable ethylenic bonds. A variety of ethylenically unsaturated reactants are suitable, so long as the reactants are capable of polymerization to yield a polymerized artificial nail structure upon exposure to the appropriate stimuli. Suitable ethylenically unsaturated reactants are disclosed in U.S. Pat. No. 6,818,207 which is incorporated by reference.

Certain embodiments of the liquid composition comprise at least one polymer which is incorporated within the 3-D lattice and which conveys enhanced adhesiveness and which confers solvent sensitivity to the polymerized lattice. The inventors have discovered that the presence of certain polymers at the polymer/nail interface, renders the interfacial bonds susceptible to rupture by organic solvents.

According to an aspect, a polymer which conveys both enhanced adhesion and which sensitizes the polymer/nail interface to solvent is a co-polymer of polymethyl methacrylate (PMMA) and polymethacrylic acid (PMAA). According to an aspect, the monomers are present in the polymer in a ratio of 90 parts PMMA to 10 parts PMAA (90:10 PMMA/PMAA). According to an aspect, the PMAA monomer fraction may vary from 0 to 100%. According to an aspect, the PMMA-PMAA copolymer has a PMMA:PMAA monomer ratio of about 50:50. According to an aspect, the PMMA-PMAA copolymer has a PMMA:PMAA monomer ratio of about 60:40. According to an aspect, the PMMA-PMAA copolymer has a PMMA:PMAA monomer ratio of about 80:20. According to an aspect, the PMMA-PMAA copolymer has a PMMA:PMAA monomer ratio of about 90:10. According to an aspect, the PMMA-PMAA copolymer has a PMMA:PMAA monomer ratio of about 95:5.

Certain embodiments of the liquid composition comprise at least one monomer which imparts to the interfacial bonds a high degree of sensitivity to organic solvent. According to an aspect, the at least one monomer may be polypropylene glycol-4-monomethacrylate (PPG-4 monomethacrylate) or polypropylene glycol-5-monomethacrylate (PPG-5 monomethacrylate). According to an aspect, suitable monomers may include any acrylated or methacrylated monomer in the polyethylene glycol (PEG), polypropylene glycol (PPG), or polybutylene glycol (PBG) families. According to an aspect, such monomers are present at from about 0 to about 70 weight % (wt %).

In certain embodiments, the monomer that imparts to the interfacial bonds a high degree of sensitivity to organic solvent may be a polyol modified urethane (meth)acrylate.

An embodiment of the present disclosure provides a polymerizable liquid composition comprised of a (meth)acrylate monomer which provides improved adhesion, viscosity, wear and durability. In certain embodiments, the (meth)acrylate monomer is a tetrahydrofurfuryl methacrylate. In other embodiments, some or all of the tetrahydrofurfuryl methacrylate may be substituted by such monomers including, but not limited to methyl or ethyl methacrylate, hydroxypropyl or hydroxybutyl methacrylate, and/or other monomers such as pyromellitic dianhydride glyceryl dimethacrylate, and similar (meth)acrylate monomers. The aromatic or aliphatic (meth)acrylate monomer may be present from about 0 to about 70 wt %.

Certain embodiments of the present disclosure may comprise another or "second" aromatic or aliphatic (meth)acrylate monomer which may be present to improve adhesion. The second (meth)acrylate monomer may be a pyromellitic dianhydride glyceryl dimethacrylate (PMGDM). In general, the second methacrylate monomer may be an acid-functional, (meth)acrylate monomer. The acid-functional, (meth)acrylate monomer may be a carboxylic acid polymer. The second methacrylate monomer may be present from about 0 to about 70 wt %.

Certain embodiments of the removable, adhesion-promoting nail coating composition of may comprise an adhesion promoter selected from the group consisting of
hydroxypropyl methacrylate (HPMA),
hydroxyethyl methacrylate (HEMA),
ethyl methacrylate (EMA),
tetrahydrofurfuryl methacrylate THFMA,
pyromellitic dianhydride di(meth)acrylate,
pyromellitic dianhydride glyceryl dimethacrylate,
pyromellitic dimethacrylate,
methacroyloxyethyl maleate,
2-hydroxyethyl methacrylate/succinate,
1,3-glycerol dimethacrylate/succinate adduct,
phthalic acid monoethyl methacrylate,
methacroyloxyethyl maleate,
2-hydroxyethyl methacrylate/succinate,
1,3-glycerol dimethacrylate/succinate adduct,
butyl methacrylate,
isobutyl methacrylate,
PEG-4 dimethacrylate,
PPG monomethacrylate,
trimethylolpropane trimethacrylate,
isopropylidenediphenyl bisglycidyl methacrylate,
lauryl methacrylate,
cyclohexyl methacrylate,
hexyl methacrylate, urethane methacrylate,
triethylene glycol dimethacrylate,
ethylene glycol dimethacrylate,
tetraethylene glycol dimethacrylate,
trimethylolpropane trimethacrylate,
neopentylglycol dimethacylate,
acetoacetoxy methacrylate,
acetoacetoxyethyl methacrylate (AAEMA),
polyetheramine,
glycidyl methacrylates
maleic anhydride
terpolymers containing vinyl acetate
organosilanes
organotitanates
chlorinated polyolefins
sucrose acetate isobutyrate caprylic/capric triglyceride
glyceryl hydrogenated rosinate
pentaerythryl hydrogenated rosinate
styrene/methyl styrene/indene copolymer
blocked isocyanate PVC
polyamidoamine PVC
and mixtures thereof.

Certain embodiments of the polymerizable liquid composition of the present disclosure may comprise a urethane (meth)acrylate resin which may convey flexibility and toughness to the polymerized product. In certain embodiments, urethane methacrylates are preferred. The urethane (meth)acrylate monomer may be present from about 0 to about 80 wt %. In certain embodiments, the urethane (meth)acrylate may have a molecular weight (grams/mole) of from about 100 to about 20,000. In certain embodiments, the urethane (meth)acrylate may have a molecular weight of from about 300 to about 15,000. In certain embodiments, the urethane (meth)acrylate may have a molecular weight of from about 500 to about 13,000. In certain embodiments, the urethane (meth)acrylate may have a molecular weight of from about 500 to about 6,000.

In certain embodiments of the disclosure, the 3-D thermoset lattice is interdispersed within a network of voids left by the evolution of a solvent. During the curing process, domains of a non-reactive, organic solvent-dissolvable resin form within the crosslinked polymer matrix. When it is desired to remove the nail covering, the polymer is exposed to a solvent which penetrates the network of voids to the domains of the solvent-dissolvable resin. Dissolution of the resin allows further penetration of solvent to the interior of the thermoset matrix and also to the polymer/nail interface.

Certain embodiments of the polymerizable liquid composition of the present disclosure may comprise a non-reactive, solvent-dissolvable polymer. According to an aspect, the non-reactive, solvent-dissolvable polymer is a cellulose ester. According to a particular aspect, the non-reactive, solvent-dissolvable polymer is a cellulose acetate alkylate. According to a more particular aspect, the non-reactive, solvent-dissolvable polymer is a cellulose acetate butyrate or a cellulose acetate propionate. The non-reactive, solvent-dissolvable polymer may be a mixture of any acceptable polymer. According to a further aspect, the non-reactive, solvent-dissolvable polymer may be present at from about 0 to about 75 wt %.

Certain embodiments of the formulation may optionally comprise resins, such as, but not limited to polyvinylbutyral and/or tosylamide formaldehyde resins. Such resins may act as film formers, adhesion promoters, and aids to removal. These resins may also qualify as solvent-dissolvable resins which are dispersed in the polymerized structure and can be easily dissolved by a solvent to facilitate solvent absorption and migration during removal.

The removable, adhesion-promoting nail coating composition may comprise a non-reactive, solvent-dissolvable polymer selected from the group consisting of ethyl tosylamide, adipic acid/fumaric acid/phthalic acid/tricyclodecane dimethanol copolymer, adipic acid/neopentyl glycol/trimellitic anhydride copolymer, phthalic anhydride/trimellitic anhydride/glycols copolymer, polyethyl cellulose, polyhydroxypropyl cellulose, polyethyl acrylate oxide, poly lactic acid, nitrocellulose, cellulose ester, and mixtures thereof.

Without being bound by theory, the present disclosure eases removal of the nail covering by facilitating entrance of solvent into the interior of the coating. Conventional polymerized nail coatings are weakened by long-term (30 to 90 minute) exposure to organic solvents. The solvent slowly seeps in at the outer surface and edges of the thermoset and eventually swells the coating. The swelling eventually weakens the entire matrix structure, as well as disrupts adhesion to the nail surface. Even a weakly attached nail coating may require surface abrasion to enhance solvent penetration and speed removal. However, the slow rate at which solvent diffuses through the thermoset, limits the rate of swelling and subsequent removal.

The present invention provides a 3-D thermoset interdispersed within a network of voids left from evolution of solvent during cure. The network of voids may be occupied by domains of organic solvent-soluble polymer. When the coating is exposed to organic solvents, the solvents penetrate the bulk material through the voids left during the curing process to the cellulose ester, or other non-reactive, organic solvent-soluble polymer, which is dissolved by the solvent, leaving further voids which allow deeper and more complete penetration into the bulk of the material down to the polymer/nail interface. The result is a series of solvent accessible passageways riddled throughout the thermoset. Under these conditions, solvent may attack the interior of the thermoset no longer limited by a slow diffusion rate.

Aspects of the present disclosure provide a basecoat as a layer intermediate between the nail and coating surfaces. The inventive basecoat is a polymerizable liquid so as to provide a completely conformal coating over the nail surface. The inventive composition may be polymerizable with actinic radiation. The actinic radiation may be ultraviolet (UV) radiation.

Aspects of the present disclosure provide a color layer as a decorative layer that may be applied to an exposed surface of an adhesive basecoat layer.

Aspects of the present disclosure provide a topcoat layer to be applied to an exposed surface of a decorative layer.

According to an aspect, the inventive coating is applied, and at least partially cured, as three, distinct layers. According to an aspect, application of any one of the layers may be omitted. According to an aspect, application of any two of the layers may be omitted. According to an aspect, only a formulation for a color layer comprises colorant agents. According to an aspect, a formulation for any of the layers may comprise colorant.

The compositions of the invention may contain from about 0.001-5% by weight of a plasticizer. The plasticizer causes the polymerized nail structure to have improved flexibility and reduced brittleness. Suitable plasticizers may be esters, low volatility solvents, or non-ionic materials such as non-ionic organic surfactants or silicones.

In certain embodiments, the removable, adhesion-promoting nail coating composition further comprises to 5 wt % of a plasticizer selected from the group consisting of esters, low volatility solvents (paraffinic hydrocarbons, butyrolactone, xylene, methyl isobutyl ketone), non-ionic surfactants, non-ionic silicones, isostearyl isononanoate, silicones, diisobutyl adipate, trimethyl pentanyl diisobutyrate, acetyl tributyl citrate, and mixtures thereof.

Suitable esters include those having the general structure RCO—OR' where RCO— represents a carboxylic acid radical and where —OR' is an alcohol residue. Preferably R and R' are fatty radicals, having 6 to 30 carbon atoms, and may be saturated or unsaturated. Examples of suitable esters are those set forth on pages 1558 to 1564 of the C.T.F.A. Cosmetic Ingredient Dictionary and Handbook, Seventh Edition, 1997, which is hereby incorporated by reference. In the preferred compositions of the invention, the plasticizer is an ester of the formula RCO—OR' wherein R and R' are each independently a straight or branched chain $C_{6-30}$ alkyl. A suitable plasticizer is isostearyl isononanoate. Other suitable plasticizers are disclosed in U.S. Pat. No. 6,818,207 which is incorporated by reference.

According to certain embodiments, the formulations may further comprise at least one UV stabilizing agent. In certain embodiments, the UV stabilizer is present at up to 2 wt %.

The compositions of the invention may contain one or more UV absorbers, which assist in reducing the yellowing which is often seen in artificial nails. UV absorbers have the ability to convert incident UV radiation into less damaging infrared radiation (heat), or visible light. A recommended amount of UV absorber is 0.001-5% by weight of the total composition. Suitable UV absorbers include hydroxy benzotriazole compounds and benzophenone compounds such as are disclosed in U.S. Pat. No. 6,818,207, incorporated by reference.

The removable, adhesion-promoting nail coating composition may comprise up to 5 wt % of a UV-absorber selected from the group consisting of hydroxy benzotriazole compounds such as 2-(2-hydroxy-5'-methylphenyl)benzotriazole, benzophenones, 1-12,3-benzylidene camphor, benzyl salicylate, borneolone, bumetrizole, PABA, butyl PABA, butyl methoxydibenzoymethane, cinoxate, DEA-methoxycinnamate, dbenzoxazoyl naphthalene, digalloyl trioleate, diisopropyl methyl cinnamate TinuvinP® and mixtures thereof.

The inventive composition comprises monomers and oligomers having a plurality of free hydroxyl groups. The hydroxyl groups of the inventive composition may be available to form hydrogen bonds with a substrate which may be a keratinous nail surface. The hydroxyl groups of the inventive composition may be available to form hydrogen bonds with a substrate which may be a surface of a natural nail or artificial nail enhancement coating.

Without being bound by theory, the present inventors eases removal of the nail covering by facilitating entrance of solvent into the interior of the coating. Conventional polymerized nail coatings are weakened by surface abrasion followed by long-term (30 to 90 minute) exposure to organic solvents. The solvent slowly seeps in at the outer surface and edges of the thermoset and eventually swells the coating. The swelling eventually weakens the entire matrix structure, as well as disrupts adhesion to the nail surface. Even a weakly attached nail coating may require abrasion to enhance solvent penetration and speed removal. However, the slow rate at which solvent diffuses through the thermoset, limits the rate of swelling.

The present invention provides a 3-D thermoset interdispersed within a network of solvent-dissolvable channels and inclusions. Upon exposure to organic solvent, the cellulose ester, or other non-reactive, organic solvent-soluble polymer, is dissolved and leached from the coating. The result is a series of solvent accessible passageways riddled throughout the thermoset. Under these conditions, solvent may attack the interior of the thermoset no longer limited by a slow diffusion rate.

In certain embodiments, the removable, adhesion-promoting nail coating composition further comprises monomers and oligomers chosen such that various bonds within the resulting thermoset are provided an increased sensitivity to solvent. In certain embodiments, such monomers and oligomers are selected from the group consisting of propoxylated allyl methacrylate, methoxy polyethylene glycol (350) monomethacrylate, polyethylene glycol (600) monomethacrylate, stearyl methacrylate, tridecyl methacrylate, hydroxyethyl methacrylate acetate, and mixtures thereof.

Certain embodiments of the disclosed polymerizable composition may be viscous gels or liquids. Gel or liquid embodiments may be polymerized by exposure to radiant energy, such as heat, visible, UV, or electron-beam radiation. Liquid or gel embodiments are applied upon nails and may be shaped to the desired configuration. The coated nails are exposed to radiant energy, and polymerization occurs.

The inventive composition may be polymerizable with actinic radiation. The actinic radiation may be visible, ultraviolet (UV), or electron beam radiation. The UV radiation may be characterized by a wavelength, or group of wavelengths, typically, but not limited to about 320 to about 420 nanometers.

After the liquid composition is applied to a nail surface, the liquid is polymerized or cured. The liquid composition comprises ethylenic unsaturated (meth)acrylates which may be polymerized or cured by a UV-initiated, free-radical polymerization method. Persons of skill in the polymerization arts may readily determine suitable photoinitiators for use with the invention. Suitable photoinitiators include, but are not limited to benzoyldiphenylsphosphinates, phenyl Ketones, and dimethyl ketals Set forth below are, non-limiting representative photoinitiators that are suitable for purposes of the invention.

A non-limiting suitable photoinitiator is a 2,4,6-trimethyl-benzoyldiphenylphosphorous derivative. A suitable derivative is ethyl-2,4,6-trimethylbenzoyldiphenylphosphinate, which may be obtained under the tradename Lucirin® TPO-L (BASF Aktiengesellschaft, Ludwigshafen, Del.). Another non-limiting suitable derivative is 2,4,6-Trimethylbenzoyl-diphenylphosphine oxide, which may be obtained under the trade name Lucerin® TPO (BASF) or as Genocure® TPO (Rahn). The 2,4,6-trimethylbenzoyldiphenylphosphinate photoinitiator may be present from about 0% to about 20 wt %.

A non-limiting suitable photoinitiator is hydroxycyclohexyl phenyl ketone, which may be obtained under the tradename Igracure® 184 and which may be present from about 0 to about 20 wt %.

A non-limiting suitable photoinitiator is benzil dimethyl ketal (BDK), which may be obtained under the tradename FIRSTCURE® BDK (Albemarle, Baton Rouge, La., US) and which may be present from about 0 to about 20 wt %.

It may be desirable to include one or more polymerization regulators. A polymerization regulator assists in preventing the polymerization of the monomer composition from occurring too quickly. Hydroquinone and similar materials are suitable polymerization regulators. Suggested ranges of polymerization regulators are from about 0.0001-5% by weight of the total composition. Suitable polymerization regulators are disclosed in U.S. Pat. No. 6,818,207, incorporated by reference.

An aspect of the disclosure provides a color layer. Certain embodiments of a color layer may comprise up to 10 wt % pigments and/or dyes. Embodiments of the basecoat and topcoat may have up to 1 wt % pigments and or dyes. High concentrations of pigments and/or dyes may absorb UV radiation. To compensate therefore, certain embodiments of the present disclosure may comprise higher concentrations, up to 20 wt %. photoinitiator.

A conventional thermoset nail coating comprises 100% solids and does not comprise non-reactive solvents. The polymerizable liquid composition of the present disclosure further comprises at least one non-reactive solvent. A suitable non-reactive solvent is readily volatile at room temperature and is a good solvent for the remaining ingredients. Upon application, the non-reactive solvent readily volatilizes leaving regions of increased porosity throughout the nail coating. These porous regions later facilitate the entry of a remover solvent which may be acetone.

Suitable non-reactive solvents may be selected from the group consisting of ketones, alkyl acetates, alcohols, alkanes, alkenes, and mixtures thereof. Suitable solvents may be selected from the group consisting of acetone, ethyl acetate, butyl acetate, isopropyl alcohol, ethanol, methyl ethyl ketone, toluene, hexane, and mixtures thereof. A particularly suitable solvent is acetone. Typically a solvent or a mixture of solvents is included at up to about 70 weight percent.

Certain embodiments of the formulation may optionally comprise (meth)acrylate monomers or polymers in order to fine tune adhesion and removal properties. Non-limiting examples of such (meth)acrylates include: mono or poly (meth)acrylic acids, hydroxypropyl methacrylate (HPMA), hydroxyethyl methacrylate (HEMA), pyromellitic dianhydride di(meth)acrylate, pyromellitic dianhydride glyceryl dimethacrylate, pyromellitic dimethacrylate, methacroyloxyethyl maleate, 2-hydroxyethyl methacrylate/succinate, 1,3-glycerol dimethacrylate/succinate adduct, phthalic acid monoethyl methacrylate, ethyl methacrylate, tetrahydrofurfuryl methacrylate, butyl methacrylate, isobutyl methacrylate, PEG-4 dimethacrylate, PPG monomethacrylate, trimethylolpropane trimethacrylate, isopropylidenediphenyl bisglycidyl methacrylate, lauryl methacrylate, cyclohexyl methacrylate, hexyl methacrylate, urethane methacrylate, triethylene glycol dimethacrylate, ethylene glycol dimethacrylate, tetraethylene glycol dimethacrylate, trimethylolpropane trimethacrylate, neopentylglycol dimethacylate, acetoacetoxyethyl methacrylate (AAEMA), and mixtures thereof.

An aspect of the present invention provides a basecoat. The unpolymerized basecoat may have the consistency of a liquid or gel. The unpolymerized basecoat may be applied to a keratin nail surface. The unpolymerized basecoat may be polymerized by exposure to UV radiation. In an embodiment the unpolymerized basecoat may be applied to a nail surface and contacted with a color layer such as is described in co-pending application Ser. No. 12/573,633. The nail surface-basecoat-color layer system may be exposed to UV radiation. The basecoat may be polymerized thereby adhering the color layer to the nail surface.

In an embodiment, the basecoat is applied without abrading the nail surface. In an embodiment, a color layer or other material may be adhered to the nail surface without abrading the nail surface. In an embodiment, a color layer or other material may be removed from the nail surface without abrading the surface of the nail coating.

In an embodiment, the removable, adhesion-promoting nail coating composition further comprises up to 10 wt % of a colorant selected from the group consisting of dyes, pigments, effects pigments, and mixtures thereof.

In certain embodiments, the removable, adhesion-promoting nail coating composition may further comprise a filler selected from the group consisting of silica, clay, metal oxide, nanosilica, nanoalumina, and mixtures thereof.

In an embodiment, the removable, adhesion-promoting nail coating composition further comprises a rheology modifier selected from the group consisting of stearalkonium hectorite, calcium aluminum borosilicate, calcium sodium borosilicate, synthetic fluorphlogopite, silica, titanium oxide, tin oxide, and mixtures thereof.

As compared to conventional artificial nail enhancement coatings, the present disclosure relates to a major advantage in that it enables the tough, rubbery color layer to adhere to the nail for periods in excess of two weeks without adhesion loss or other signs of breakdown of the coating. In contrast to conventional coatings, the present disclosure relates to a UV gel system that is less damaging to the nail, since the application process requires no abrasive filing of the nail. And the process of removal at most calls for the use of a light touch of a wooden stick. The present basecoat is removable without any abrasion of the uppermost layers if they are solvent-removable themselves. Moreover, in comparison to conventional systems, the present disclosure relates to a more rapidly removable basecoat system achieving removal in as quickly as 20 seconds for basecoat alone to up to about 20 minutes for the whole system.

Polymerizable basecoats may adhere to the keratin nail surface by means of hydrogen and/or covalent bonds. The basecoat may be removed from the nail surface by means of organic solvents. Non-limiting solvents include acetone, butyl acetate, isopropyl alcohol, ethanol, ethyl acetate, methyl acetate, methyl ethyl ketone, and mixtures thereof.

Certain embodiments of the formulation may optionally comprise plasticizers, such as, but not limited to diisobutyl adipate. Plasticizers act to minimize the effects of brittleness of the subsequently formed polymer after exposure to UV radiation, sun light, or air. Plasticizers also are found to slightly shorten the removal time. Plasticizers may be present at from 0 to about 25 wt %. Persons of skill in the polymer arts will appreciate that inclusion of plasticizers above a certain limit is undesirable because they may impair the integrity and durability of the coatings.

The unpolymerized color layer may have the consistency of a liquid or gel. The unpolymerized color layer may be applied to an polymerized basecoat surface. In an embodiment the polymerized basecoat may be an embodiment of co-pending application Ser. No. 12/555,571. The polymerized basecoat may be applied to a nail surface and contacted with a color layer. The nail surface-basecoat-color layer system may be exposed to UV radiation. The basecoat and color layer may be polymerized thereby adhering the color layer to the nail surface.

In an embodiment, a color layer may be removed from the nail surface without abrading the nail surface.

As compared to conventional nail coatings, the present disclosure relates to a major advantage in that it enables the durable color layer to adhere to the nail for periods in excess of two weeks without breakdown of the coating. In contrast to conventional coatings, the present disclosure relates to a UV gel system that is non-damaging to the nail. The application process requires no abrasive treatment of the nail and the process of removal at most calls for the use of a light touch of a wooden stick. Moreover, in comparison to conventional systems, the present disclosure relates to a more rapidly removable nail coating system achieving removal in as quickly as 20 seconds for basecoat alone to up to 20 minutes for the whole system.

The polymerized basecoat of the present invention may adhere to the keratin nail surface by means of hydrogen bonds. The basecoat and color layer may be removed from the nail surface by means of organic solvents. Non-limiting solvents include acetone, butyl acetate, isopropyl alcohol, ethanol, ethyl acetate, methyl ethyl ketone, and mixtures thereof.

EXAMPLE 1

Chemical Resistance Test

To compare chemical resistance a topcoat formulation according to the present disclosure was compared against a commercial polish topcoat formulation and a commercial enhancement type topcoat formulation. We employed the conventional MEK double rub test except that acetone substituted for the methyl ethyl ketone. Thin films of each formulation were prepared on glass microscope slides. Each film was formed to a 5 mil wet thickness. The commercial enhancement type formulation and the formulation of the present disclosure were cured by exposure to UV light using a Brisa™ lamp. A very thin, unpolymerized tacky top layer was wiped to dryness using 99 wt % isopropanol. The polish formulation was not cured, but was dried under ambient conditions. All specimens were aged under conditions of ambient light and temperature for 24 hours. Following aging, each sample was individually rubbed with cotton pads soaked in 99 wt % acetone. The polish formulation was completely removed by one cycle, a cycle being defined as two rubs, one in each direction. The formulation of the present invention was dulled by one cycle, but remained intact for at least 75 cycles. The enhancement formulation remained shiny and intact for at least 100 cycles.

EXAMPLE 2

Pencil Hardness Test

To test scratch resistant, we recorded the lowest "H" number of the pencil which dented test samples prepared as given in Example 1. We also recorded the lowest "H" number of the pencil capable of tearing test films. The polish formulation was dented and torn by 3 H and 4 H pencils, respectively. The formula of the present disclosure was dented and torn respectively by 3 H and 6 H pencils. The enhancement formula was dented by a 4 H pencil and was not torn even by the hardest pencil (6 H). This test showed that the present disclosure had a significant better scratch resistance than the nail polish formula.

Industrial Utility

This invention has industrial applicability in providing compositions and methods for improving the adhesion of nail coatings to nails without requiring abrasion of the nail. The invention further provides means for removing a nail coating without requiring extended soak times or abrasion of the nail surface.

The invention claimed is:

1. The removable, adhesion-promoting nail coating composition comprising a polymerizable (meth)acrylate, a urethane (meth)acrylate resin and an adhesion promoter selected from the group consisting of:
hydroxypropyl methacrylate (HPMA),
hydroxyethyl methacrylate (HEMA),
ethyl methacrylate (EMA),
tetrahydrofurfuryl methacrylate THFMA,
pyromellitic dianhydride di(meth)acrylate,
pyromellitic dianhydride glyceryl dimethacrylate (PMGDM),
pyromellitic dimethacrylate,
methacroyloxyethyl maleate,
2-hydroxyethyl methacrylate/succinate,
1,3-glycerol dimethacrylate/succinate adduct,
phthalic acid monoethyl methacrylate,
butyl methacrylate,
isobutyl methacrylate,
PEG-4 dimethacrylate,
PPG monomethacrylate,
trimethylolpropane trimethacrylate,
isopropylidenediphenyl bisglycidyl methacrylate,
lauryl methacrylate,
cyclohexyl methacrylate,
hexyl methacrylate,
urethane methacrylate,
triethylene glycol dimethacrylate,
ethylene glycol dimethacrylate,
tetraethylene glycol dimethacrylate,
trimethylolpropane trimethacrylate,
neopentylglycol dimethacylate,
acetoacetoxy methacrylate,
acetoacetoxyethyl methacrylate, (AAEMA)
polyetheramine,
glycidyl methacrylates,
maleic anhydride,
terpolymers containing vinyl acetate,
organosilanes,
organotitanates,
chlorinated polyolefins,
sucrose acetate isobutyrate,
caprylic/capric triglyceride,
glyceryl hydrogenated rosinate,
pentaerythryl hydrogenated rosinate,
styrene/methyl styrene/indene copolymer,
blocked isocyanate PVC,
polyamidoamine PVC,
and mixtures thereof;
wherein the polymerizable (meth)acrylate is different from the adhesion promoter, and the urethane (meth)acrylate resin is different from the adhesion promoter,
wherein said composition cures to a thermoset, and
removal of the cured coating from a nail surface upon exposure to an organic solvent is achieved in less than 20 minutes without abrading the coating or nail surface.

2. The removable, adhesion-promoting nail coating composition according to claim 1, further comprising a solvent-sensitivity enhancing monomer or oligomer and a non-reactive, solvent-dissolvable polymer.

3. The removable, adhesion-promoting nail coating composition of claim 2, wherein said non-reactive, solvent-dissolvable polymer is selected from the group consisting of:
cellulose esters,
polyvinylbutyral resins,
tosylamide (toluensulfonamide) formaldehyde resins,
ethyl tosylamide,
adipic acid/fumaric acid/phthalic acid/tricyclodecane dimethanol copolymer,
adipic acid/neopentyl glycol/trimellitic anhydride copolymer,
phthalic anhydride/trimellitic anhydride/glycols copolymer,
polyethyl cellulose,
polyhydroxypropyl cellulose,
polyethyl acrylate oxide,
poly lactic acid,
nitrocellulose,
and mixtures thereof.

4. The removable, adhesion-promoting nail coating composition of claim 3, wherein said cellulose ester is selected from the group consisting of cellulose acetate butyrate, cellulose acetate propionate, and mixtures thereof.

5. The removable, adhesion-promoting nail coating composition of claim 1, wherein said polymerizable (meth)acrylate is a polyol modified (meth)acrylate.

6. The removable, adhesion-promoting nail coating composition of claim 5, wherein said polyol modified (meth)acrylate is a polyol modified urethane (meth)acrylate.

7. The removable, adhesion-promoting nail coating composition of claim 1, wherein said polymerizable (meth)acrylate is a polyalkyleneglycol modified (meth)acrylate.

8. The removable, adhesion-promoting nail coating composition of claim 1, further comprising at least one PMMA-PMAA copolymer.

9. The removable, adhesion-promoting nail coating composition of claim 1, wherein the adhesion promoter comprises at least one PMGDM.

10. The removable, adhesion-promoting nail coating composition of claim 1, wherein said thermoset remains intact to at least 150 acetone double rubs.

11. The removable, adhesion-promoting nail coating composition of claim 1, further comprising a non-reactive solvent.

12. The removable, adhesion-promoting nail coating composition of claim 2, wherein said solvent-sensitivity enhancing monomer or oligomer is selected from the group consisting of:
   polyethylene glycol (meth)acrylates,
   polypropylene glycol (meth)acrylates,
   polybutylene glycol (meth)acrylates,
   propoxylated allyl methacrylate
   methoxy polyethylene glycol (350) monomethacrylate,
   polyethylene glycol (600) monomethacrylate,
   stearyl methacrylate,
   tridecyl methacrylate,
   hydroxyethyl methacrylate acetate,
   and mixtures thereof;
   wherein the solvent-sensitivity enhancing monomer or oligomer is different from the adhesion promoter.

13. The removable, adhesion-promoting nail coating composition of claim 1, further comprising up to 5 wt % of a plasticizer.

14. The removable, adhesion-promoting nail coating composition of claim 13, wherein said plasticizer is selected from the group consisting of:
   esters,
   low volatility solvents
   paraffinic hydrocarbons
   butyrolactone,
   xylene,
   methyl isobutyl ketone,
   non-ionic surfactants,
   non-ionic silicones,
   isostearyl isononanoate,
   silicones,
   diisobutyl adipate,
   trimethyl pentanyl diiisobutyrate,
   acetyl tributyl citrate,
   and mixtures thereof.

15. The removable, adhesion-promoting nail coating composition of claim 1, further comprising up to 10 wt % of a photoinitiator.

16. The removable, adhesion-promoting nail coating composition of claim 15, wherein said photoinitiator is selected from the group consisting of ethyl trimethylbenzoyl phenylphosphinate, 2,4,6-trimethylbenzoyldiphenylphosphine oxide, hydroxycyclohexyl phenyl ketone, benzyl dimethyl ketal, and mixtures thereof.

17. The removable, adhesion-promoting nail coating composition of claim 1, further comprising up to 5 wt % of a UV-absorber.

18. The removable, adhesion-promoting nail coating composition of claim 17, wherein said UV-absorber is selected from the group consisting of:
   hydroxy benzotriazole compounds,
   2-(2-hydroxy-5'-methylphenyl)benzotriazole,
   benzophenones 1-12,
   3-benzylidene camphor,
   benzyl salicylate,
   borneolone,
   bumetrizole,
   PABA,
   butyl PABA,
   butyl methoxydibenzoymethane,
   cinoxate,
   DEA-methoxycinnamate,
   dibenzoxazoyl naphthalene,
   digalloyl trioleate,
   diisopropyl methyl cinnamate,
   and mixtures thereof.

19. The removable, adhesion-promoting nail coating composition of claim 1, further comprising a filler.

20. The removable, adhesion-promoting nail coating composition of claim 19, wherein said filler is selected from the group consisting of silica, metal oxide, nanosilica, nanoalumina, and mixtures thereof.

21. The removable, adhesion-promoting nail coating composition of claim 1, further comprising up to 10 wt % of a colorant.

22. The removable, adhesion-promoting nail coating composition of claim 21, wherein said colorant is selected from the group consisting of dyes, pigments, effects pigments and mixtures thereof.

23. The removable, adhesion-promoting nail coating composition of claim 1, further comprising a rheology modifier.

24. The removable, adhesion-promoting nail coating composition of claim 23, wherein said rheology modifier is selected from the group consisting of:
   stearalkonium hectorite,
   calcium aluminum borosilicate,
   calcium sodium borosilicate,
   synthetic fluorphlogopite,
   silica,
   titanium oxide,
   tin oxide,
   and mixtures thereof.

25. A method of providing ease of removal of a cured nail coating comprising adding at least one solvent-sensitivity enhancing monomer or oligomer that is an acrylated or methacrylated monomer of polyethyleneglycol (PEG), polypropyleneglycol (PPG), or polybutyleneglycol (PBG) to the nail coating composition of claim 1 before curing.

26. The removable, adhesion-promoting nail coating composition of claim 1, wherein the polymerizable (meth)acrylate is selected from the group consisting of hydroxypropyl methacrylate and hydroxyethyl methacrylate.

27. The removable, adhesion-promoting nail coating composition of claim 1, wherein the polymerizable (meth)acrylate is hydroxypropyl methacrylate.

28. The removable, adhesion-promoting nail coating composition of claim 1, wherein the polymerizable (meth)acrylate is hydroxyethyl methacrylate.

29. The removable, adhesion-promoting nail coating composition of claim 1, wherein the adhesion promoter is selected from the group consisting of hydroxypropyl methacrylate, hydroxyethyl methacrylate and tetrahydrofurfuryl methacrylate (THFMA).

30. The removable, adhesion-promoting nail coating composition of claim 1, wherein the adhesion promoter is tetrahydrofurfuryl methacrylate (THFMA).

31. The removable, adhesion-promoting nail coating composition of claim 1, wherein the polymerizable (meth)acrylate and the adhesion promoter are hydroxypropyl methacrylate and hydroxyethyl methacrylate, respectively.

32. The removable, adhesion-promoting nail coating composition according to claim 1, further comprising a non-reactive, solvent-dissolvable polymer.

33. The removable, adhesion-promoting nail coating composition of claim 32, wherein said non-reactive, solvent-dissolvable polymer is selected from the group consisting of:
cellulose esters,
polyvinylbutyral resins,
tosylamide (toluensulfonamide) formaldehyde resins,
ethyl tosylamide,
adipic acid/fumaric acid/phthalic acid/tricyclodecane dimethanol copolymer,
adipic acid/neopentyl glycol/trimellitic anhydride copolymer,
phthalic anhydride/trimellitic anhydride/glycols copolymer,
polyethyl cellulose,
polyhydroxypropyl cellulose,
polyethyl acrylate oxide,
poly lactic acid,
nitrocellulose,
and mixtures thereof.

34. The removable, adhesion-promoting nail coating composition of claim 33, wherein said cellulose ester is selected from the group consisting of cellulose acetate butyrate, cellulose acetate propionate, and mixtures thereof.

* * * * *